United States Patent [19]

Favre

[11] Patent Number: 5,247,156

[45] Date of Patent: Sep. 21, 1993

[54] APPARATUS FOR MEASURING PHYSICAL PROPERTIES OF FLUIDS

[75] Inventor: Pierre Favre, Villars-Mendraz, Switzerland

[73] Assignee: Cableries et Trefileries de Cossonay S.A., Cossonay-Gare, Switzerland

[21] Appl. No.: 908,314

[22] Filed: Jul. 3, 1992

[51] Int. Cl.$^5$ .................... H05B 1/00; G01N 27/26
[52] U.S. Cl. .................................. 219/209; 204/425
[58] Field of Search ............... 219/209, 210; 204/424, 204/425; 123/434, 676, 697, 685

[56] References Cited

U.S. PATENT DOCUMENTS

| | | | |
|---|---|---|---|
| 4,462,890 | 7/1984 | Touda | 204/425 |
| 4,464,244 | 8/1984 | Uchida | 204/424 |
| 4,561,402 | 12/1985 | Nakano | 123/489 |
| 4,639,305 | 1/1987 | Shibata | 204/424 |
| 4,754,119 | 6/1988 | Knauss | 219/511 |
| 4,980,557 | 12/1990 | Myers | 250/423 R |
| 5,111,792 | 5/1992 | Nagai | 123/697 |

Primary Examiner—Bruce A. Reynolds
Assistant Examiner—Michael D. Switzer
Attorney, Agent, or Firm—Martin Smolowitz

[57] ABSTRACT

The apparatus is comprised of two sensors of the thermal type (11a, 11b) made of materials resisting without any alteration to a temperature of 650° C. Probes (15a, 15b) are controlled by a microprocessor (16) to come periodically and momentarily in contact with the sensors in order to calculate (through microprocessor (16)) the thermal time constant of the sensors presenting a deposition layer of environmental polutants. The microprocessor (16) compares the value of the time constant with an order value that commands the closure of a shunt switch (17) of a resistance (18) which, when short-circuited, determines a reinforced heating of the sensors to bring them to a temperature of incineration of organic materials originating from the pollution of the ambient medium and deposited on said sensors. Thus, the sensors are maintained in the cleanliness conditions of their surface, thereby providing for the accuracy of information supplied by the sensors outside cleaning periods.

8 Claims, 2 Drawing Sheets

FIG. 1
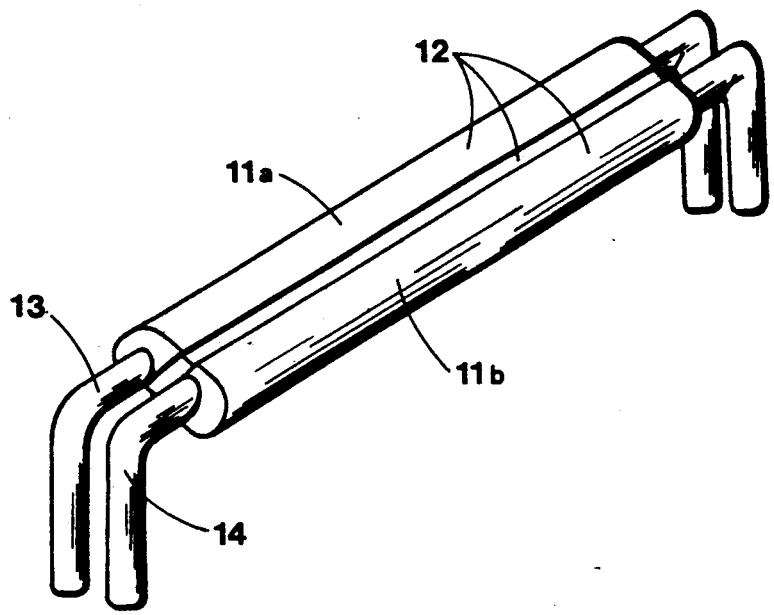
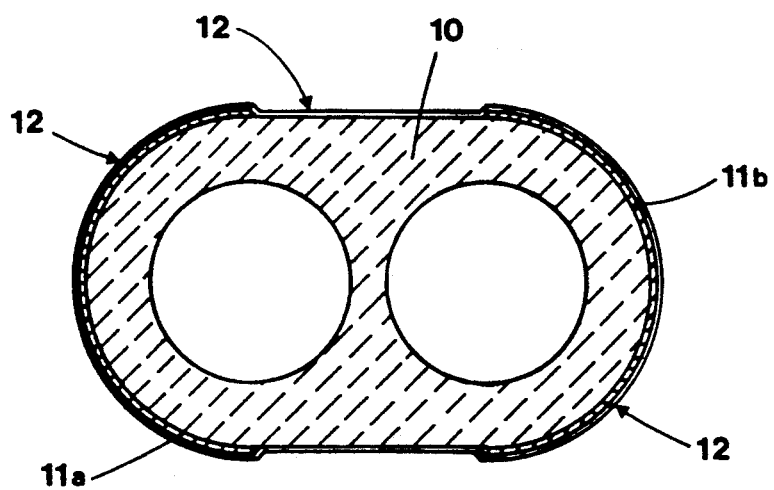
FIG. 2

APPARATUS FOR MEASURING PHYSICAL PROPERTIES OF FLUIDS

BACKGROUND OF THE INVENTION

This patent pertains to sensor apparatus for measuring the physical properties of fluids, and particularly to thermal type anemometric sensors adapted for conveniently eliminating undesired deposits of polluting substances on the sensor surface.

Numerous sensors are known, for example moisture sensors, temperature sensors, and thermal effect sensors such as those used in anemometry. However, when these sensors are used in an environment (generally, the atmosphere) loaded with polluting substances (e. g. hydrocarbons and smoke), this pollution causes deposits of polluting substances on the surface of the sensors, the effect of which is that the measurements to be carried out are adversely affected.

THE INVENTION

The invention is aimed at providing a solution which makes it possible to eliminate this detrimental effect of ambient pollution on the accuracy of the measurements carried out by means of sensors intended to be used in a polluted environment.

The object of the present invention is in accordance with claim 1.

In the following, the invention is contemplated mainly, but not exclusively, for the case of thermal anemometric sensors.

The performances of thermalanemometers described in numerous patents: U.S. Pat. No. 4,206,638 (1980)—U.S. Pat. No. 4,279,147 (1981)—U.S. Pat. No. 4,793,182 (1988)—U.S. Pat. No. 4,794,795 (1989)—U.S. Pat. No. 4,936,144 (1990)—U.S. Pat. No. 4,920,793 (1990) and in reference works such as "Resistance Temperature Transducers" by Virgil A. Sandbord, Colorado State University and "Hitzdraht- und Hitzfilmanemometrie" by Dr. Ing. Herbert Strickert, are more or less altered by the presence of contaminating agents. This is due to the fact that the thermal exchange is related to the physical properties of the layer formed on the interface between the resistive sensor and air.

Thus, the thermal conductivity, the specific heat, the thickness, the rugosity and other further properties alter the thermal exchange law between the sensor and air.

In its principle, the directly or indirectly heated thermal anemometric sensor is based on the thermal exchange from a heated element which is cooled by the forced convection of the moving fluid.

In the case of directly heated thermal anemometers, by far the most common, the removal of the contaminating agents deposited on the sensor can be achieved by modifying the heating of the sensor in such a manner that the temperature of the sensor reaches the temperature of 600° C.

This raised heating can be controlled without great difficulty, by increasing the current flowing through the sensor, but it is clear that the sensor must be made of materials supporting without alteration temperatures in the order of 600° to 650° C., without the performances, in particular the stability of the resistance and of its temperature coefficient being altered.

The invention is applicable without any technological difficulties to the case of an omnidirectional thermal anemometric sensor. In the case of the directional anemometric sensor, this is more difficult. However, for example, the split-film sensor described in the U.S. Pat. No. 4,794,795 to Djorup is perfectly well suited for use within the framework of the present invention.

BRIEF DESCRIPTION OF THE DRAWINGS

The appended drawing shows, by way of example, one embodiment of the apparatus according to the invention, in the non limiting particular case of the directional anemometric sensor based on thermal loss, described in Swiss patent CH 638618 (and the corresponding patents in other countries, and in particular the U.S. Pat. No. 4,279,147).

FIG. 1 is a perspective view of the sensor according to this example.

FIG. 2 is a cross-sectional view of the sensor according to FIG. 1, shown at an enlarged scale.

PREFERRED EMBODIMENT OF THE INVENTION

Figure 3:
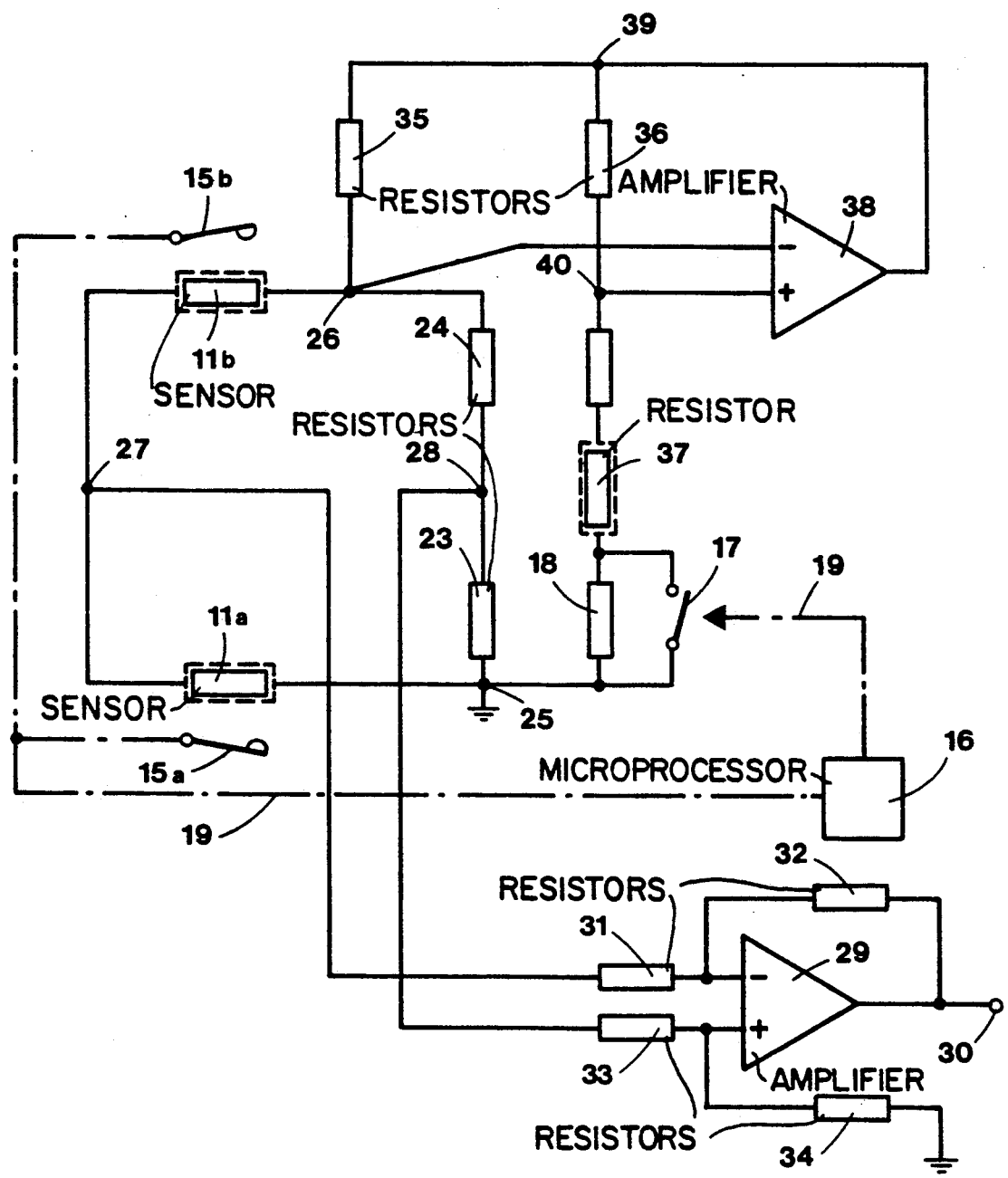
FIG. 3 is a circuit diagram of the apparatus.

The sensor, which is of the type shown in FIG. 5 of U.S. Pat. No. 4,794,795, is shaped as a hollow body 10 made of insulating ceramic material and onto which are fastened two parallel semi-cylindrical sensors 11a, 11b, which are resistive thermal sensors The sensors are coated with a protective layer 12, for example made of fused silica or of aluminium oxide.

The sensors are made of a metal, the electrical resistance and the temperature coefficient of which are not altered by the effect of heating to 600°-650° C. Platinum is an example of such a metal.

At 13 and 14, one can see the rigid support members of the sensor.

All other technical informations relating to such a sensor will be found in the above-mentioned Swiss patent CH 638618, and will not be repeated here.

The example of the apparatus according to the invention comprises one or several sensors according to FIGS. 1 and 2 and its circuit diagram is shown in FIG. 3. This diagram is directly derived from that in FIG. 3 of the above-mentioned patent CH 638618, with provides an important new addition, namely means for making possible the automatic self-cleaning of the sensors 11a, 11b, through the automatic removal of the deposits of polluting material on the sensor, to ensure that the measurements remain accurate and constant.

We shall briefly describe the part of the diagram according to FIG. 3, which is drawn from the above-mentioned Swiss patent, in order to facilitate the understanding of the invention.

The circuit according to FIG. 3 produces speed and direction signals in the form of a single composite output signal. The pair of sensors 11a and 11b is mounted in two of the four arms of a Wheatstone bridge provided with the resistances 23 and 24 used for balancing the bridge when the fluid around the sensor is at rest or when its speed is nil. The bridge of FIG. 3 is energized via the connections 25 and 26, and the balance of the bridge is measured between points 27 and 28 and then amplified with a differential amplifier 29, which thus produces a signal 30 which is a measurement of the unbalance of the bridge determining the direction. Signal 30 indicates the unbalance by assuming a polarity either positive or negative, when one or the other of the sensors 11a and 11b of the pair receives the flow of fluid at a higher speed. At the sensor protected from the flow, the speed of the flow will appear as being lower, because of the screen formed by the sensor directly exposed to the flow. The magnitude of the resulting differential output signal 30 is a direct measurement of the speed. The resistances 31 and 33 are the input resistances of the amplifier 29 and the resistances 32 and 34 are the feedback resistances. The differential amplification factor is determined by the ratio of the feedback resistances 32 and 34 to the input resistances 31 and 33, respectively. The amplification factor amounts typically to 20–25 for a maximum flow of, for example, 20 m/sec.

The bridge formed of the resistances 23 and 24 with the pair of sensors 11a and 11b, can be considered from the electrical standpoint as one single resistance which in turn becomes one arm of a second Wheatstone bridge comprised of a power resistance 35 series connected with the first Wheatstone bridge, which determines the direction, and of the resistances 36 and 37 used for balancing the second bridge at a working point defined by the value of the resistances 36 and 37. Each resistance 36 and 37 can be modified when designing the bridge circuit, or a potentiometer or a variable resistance can be used for one or the other of these resistances.

It is preferable not to use potentiometers for the two resistances. This enables the operator to choose the working point, the power level and the sensitivity of the instrument. The amplifier 38 is of the differential type, it has an amplification factor with a high output current and is mounted in a feedback mode with respect to the bridge at point 39. The input of the amplifier 38 is connected between the points 26 and 40 of the bridge and care must be taken regarding the phase, to ensure a negative feedback and not a positive feedback The sensors 11a and 11b with the resistances 23 and 24 appear to the amplifier 38 as forming a single resistance, which is modified at each variation of its component parts. In fact, the sensors 11a and 11b are resistances, with a temperature coefficient which is not nil and they undergo an internal heating, and when the film is made of platinum, they exhibit a high positive thermal coefficient. This makes it possible to choose the values of the resistances 36 and 37 in such a manner that the resistance values balancing the bridge are satisfied when the overall series-parallel resistance of the bridge for the direction, viewed as a single equivalent resistance, together with the power resistance 35, balance the resistances 36 and 37, because the same resistance ratios are established on both sides of the bridge. The active side comprises the resistance 35 with the bridge for the direction, comprised of the resistances 11a and 11b together with the resistances 23 and 24. The reference side of the bridge controlled by feedback, comprises the resistances 36 and 37.

When the sensors 11a and 11b are cold or out of operation, their resistance is lesser than when in operation and by controlling their working value through the adjustment of the ratio of the reference resistances, the values of the heated resistances necessary for balancing the bridge can be selected, all this being controlled via the feedback through the amplifier 38 to the bridge at point 39. The feedback acts so as to regulate automatically the current flowing through all the combined bridges until the resistances of the sensors 11a and 11b reach the values balancing the bridge. A small offset voltage should appear at the output of the amplifier 38 when the circuit is switched on for the first time and the sensors 11a and 11b are at room temperature, so that the first current of the bridge, which is obtained as the result of the offset voltage, is sufficient for a small error signal to appear between points 26 and 40, thus enabling the circuit to establish itself the working conditions. The working conditions indicated above were described as those of the constant temperature method (constant resistance) for a hot film or a hot wire anemometer.

The resistance 37 can be a temperature sensitive resistance which is positioned in such a manner as to measure the temperature of the ambient fluid. If the temperature coefficient of the resistance of resistance 37 is selected correctly, the working level of the bridge can be adjusted automatically in such a manner as to follow the ambient temperature, the sensors 11a and 11b thus working with a constant temperature differences with respect to ambient temperature. These working conditions make it possible to obtain a constant sensitivity for the speed of the fluid, whatever may be the ambient temperature.

The resulting surface temperature of the sensors 11a and 11b will be in the order of 125° to 135° C.

The output 30 is bipolar and indicates which sensor 11a or 11b is facing the direction of the flow. The sensor facing the flow will have, owing to its cooling, a resistance lower than the sensor protected from the flow, which detector is cooled to a lesser extent and therefore exhibits a higher resistance, while their series added resistance remains constant The magnitude of the output 30 is not linear with respect to the speed of the arriving fluid, and it indicates the amount of heat lost in the flow of fluid.

Amplifiers with 29 and 38 can be operational amplifiers power supplied from positive and negative sources. The 15 Volt power supply makes it possible to obtain a signal magnitude of at least 10 Volts at the output 30. When two bridge circuits or more, similar to those of FIG. 3, are used with a circuit of two sensors or more, a proper connection to the earth and to the power supply is necessary to avoid an undesirable interaction between the sensors and the errors which would result therefrom. The amplifiers 29 and 38 can also be of the type using a single voltage supply, e. g. 15 or 20 Volts. In this case, the +input of the amplifier 29 can be offset in the positive direction, the adjustment to zero when the speed is nil being offset accordingly to a determined positive value at the output 30.

One will find in the above-mentioned Swiss patent No. CH 638618 and in its corresponding U.S. patent, examples of numerical values for the resistances indicated in FIG. 3.

The circuit diagram of the apparatus according to the example of the present invention differs from that in FIG. 3 of the Swiss patent CH 638618 by the following.

The broken lines 19 of FIG. 3 indicate operative connections.

With each one of the sensors 11a, 11b, there is associated a probe 15a, 15b, controlled by a microprocessor 16 to come in contact with these sensors, to determine with the help of the microprocessor 16 the thermal time constant of each one of these sensors and to start a self-cleaning operation of these sensors by incineration, if this time constant is equal to or above a set value. This operation is initiated by the microprocessor, which causes the closing of a switch 17 bypassing the resistance 18 which is series connected with the resistance 37. When the resistances 18 and 37 are both in operation, they ensure that the normal heating current is supplied to the sensors 11a, 11b, whereas when resistance 18 is bypassed via the switch 17, the current received by these sensors is much higher and raises the temperature of these sensors to approximately 600° C. for a short moment. This heating ensures the self-cleaning by the incineration of the deposits of pollutants on these sensors and hence their reconditioning, so that they may supply accurate informations concerning the speed of the air to be measured with the apparatus.

The measure of the rise time (indicial response) of the current flowing through the sensor is a measurement of the thermal response time and therefore a measurement of the degree of pollution of the sensor element.

In one version of the example of the apparatus which has just been described, the control of the switch 17 for starting the self-cleaning phase by incineration could be carried out periodically by using a timer set according to the level of pollution of the ambient medium, when this level remains substantially constant. The timer would thus replace the probes 15a, 15b and the microprocessor 16.

In yet another version corresponding to the case of a pollution of the ambient medium which is low and constant, the control of the self-cleaning phases could be carried out simply by means of a manual switch 17 operated at intervals of time prescribed according to the degree of pollution.

Although the example described corresponds to the case of one type of thermal sensor, the invention is not restricted to that example. The invention encompasses all types of thermal sensors, whether heated directly or indirectly, as well as other sensors such as temperature or humidity sensors.

The self-cleaning at raised heating can be achieved by direct heating.

In the described case of the direct heating, it is anticipated that the electrical components which could be altered by this cleaning current will be bypassed before switching on the cleaning current.

One will understand from the description of FIG. 3 that the spacing of the self-cleaning operations is determined from the measurement of the thermal time constant of the sensors, since their contamination acts to increase this constant.

I claim:

1. An apparatus for measuring physical properties of fluids, comprising at least one sensor made of materials capable of supporting without any alteration a temperature 650° C., characterized in that the apparatus comprises a self-cleaning device (15a, 15b, 16–19) for incinerating polluting substances deposited from an ambient fluid on at least one sensor and altering the physical properties of the interface resistive sensor/fluid in the apparatus, and wherein this self-cleaning device includes a heating means (15a, 15b) for the sensor (11a, 11b) to heat momentarily to a temperature ensuring the rapid incineration of the polluting substances deposited thereupon and electrical control means (16, 17, 18, 19) of said heating means (15a, 15b), operating according to the state of pollution of the surface of the sensor.

2. An apparatus according to claim 1 and in which the sensor (11a, 11b) is a thermal type, for measuring temperature effects, characterized in that said electrical control means of said heating means for the cleaning include an additional electrical resistance (18) series connected with an electrical heating member (15a, 15b) of the sensor, designed for ensuring the heating of the sensor to the temperature at which the physical properties of the ambient fluid are measured, and further comprise a switch (17) for bypassing the additional resistance (18) during the self-cleaning phases by incineration, to produce at that time the additional heating of the sensor necessary for cleaning by incineration.

3. An apparatus according to claim 1, characterized in that the electrical control means of said heating means for the cleaning include an adjustable timer to operate periodically said switch (17) bypassing said additional resistance (18) at intervals of time set according to the state of pollution of the ambient fluid, in order to ensure that the automatic self-cleaning is carried out in due time.

4. An apparatus according to claim 1, characterized in that said electrical control means include a probe (15a, 15b) designed for coming in contact periodically and automatically with the resistive sensor (11a, 11b) and for co-operating simultaneously with a circuit (16–19) designed for measuring the thermal time constant of this sensor (11a, 11b) covered with a layer of deposited polluting substances, in order to carry out the cleaning operation by incineration of this layer, when the value measured for this time constant reaches or exceeds a value set in advance.

5. An apparatus according to claim 1, characterized in that the electrical control means of said additional heating means include a manual control for said switch (17) to bypass this additional resistance (18).

6. An apparatus according to claim 2, characterized in that the electrical control means of said heating means for the cleaning include an adjustable timer to operate periodically said switch (17) bypassing said additional resistance (18) at intervals of time set according to the state of pollution of the ambient fluid in order to insure that the automatic self-cleaning is carried out in due time.

7. An apparatus according to claim 2, characterized in that said electrical control means include a probe (15a, 15b) designed for coming in contact periodically and automatically with the resistive sensor (11a, 11b) for co-operating simultaneously with a circuit (16–19) designed for measuring the termal time constant of this sensor (11a, 11b) covered with a layer of deposited poluting substances, in order to carry out the cleaning operation by incineration of this layer, when the value measured for this time constant reaches or exceeds a value set in advance.

8. An apparatus according to claim 2, characterized in the electrical control means of said additional heating means include a manual control for said switch (17) to bypass this additional resistance (18).

* * * * *

UNITED STATES PATENT AND TRADEMARK OFFICE
CERTIFICATE OF CORRECTION

PATENT NO. : 5,247,156
DATED : September 21, 1993
INVENTOR(S) : Pierre Favre

It is certified that error appears in the above-indentified patent and that said Letters Patent is hereby corrected as shown below:

On the title page: Item [30] "Foreign Application Priority Data" should read -- November 13, 1990 [CH] Switzerland 3594/90-0 PCT CH91/00227 11/5/91 --.

Signed and Sealed this

Twenty-fourth Day of May, 1994

Attest:

BRUCE LEHMAN

Attesting Officer     Commissioner of Patents and Trademarks